United States Patent [19]

Segall et al.

[11] Patent Number: 4,923,442

[45] Date of Patent: May 8, 1990

[54] BLOOD SUBSTITUTE

[75] Inventors: Paul E. Segall; Harold D. Waitz; Hal Sternberg, all of Berkeley, Calif.

[73] Assignee: Cryomedical Sciences Inc., Bethesda, Md.

[21] Appl. No.: 343,850

[22] Filed: Apr. 26, 1989

Related U.S. Application Data

[63] Continuation-in-part of Ser. No. 189,011, May 2, 1988.

[51] Int. Cl.$^5$ .................... A61K 31/70; A61K 53/06; A61K 33/14; A61K 31/715

[52] U.S. Cl. ........................ 604/52; 604/49; 604/51; 128/897; 128/898; 514/23; 514/56; 514/59; 424/677; 424/679; 424/680; 424/681; 424/682; 424/692

[58] Field of Search .............. 424/677, 679, 680, 681, 424/682, 692; 514/23, 56, 59; 128/897, 898; 604/49, 51, 52, 53

[56] References Cited

PUBLICATIONS

Kelbanoff et al. "Temporary Suspension of Animation Using Total Body Perfusion and Hypothermia", *Cryobiology* 6(2) 1969, pp. 121-125.

Haff et al., "Asanguineous Hypothermic Perfusion as a Means of Total Organism Preservation", J. of Surg. Res. 19, 1975, pp. 13-19.

Belzer et al., "Combination Perfusion-Cold Storage for Optimum Cadaver Kidney Function & Utilization", Transplantation 39(2) 1985, pp. 118-121.

Wall et al., "Simple Hypothermic Preservation for Transporting Human Livers Long Distances for Transplantation", Transplantation 23(3), 1977, pp. 210-216.

Gan et al., "Ice Cold Blood-Substituted Hamsters Revive", Federation Proceedings 44(3): 623 (1985).

*Primary Examiner*—Johnnie R. Brown
*Assistant Examiner*—Jean C. Witz
*Attorney, Agent, or Firm*—Elliott L. Fineman

[57] ABSTRACT

A blood substitute suitable for replacing blood in mammalian subjects when performance of surgical procedures at hypothermic temperatures is described. The blood substitute comprises water, electrolytes at physiological concentration, dextran 40 at a concentration sufficient for the blood substitute to achieve a colloidal suspension having a fluid osmotic pressure essentially equivalent to mammalian plasma, HEPES buffer at a physiological pH, dextrose, magnesium ion at a concentration of about 0.01M and potassium ion at a concentration greater than 10 mEq per liter sufficient to prevent or arrest cardiac fibrillation. In one embodiment the blood substitute is a multi-solution system wherein the solutions comprise differing levels of the above-indicated components and are administered sequentially to completely replace a subjects circulating blood.

26 Claims, No Drawings

BLOOD SUBSTITUTE

This application is a Continuation-in-part application of U.S. patent application Ser. No. 07/189,011 filed May 2, 1988.

FIELD OF THE INVENTION

The present invention relates to the field of blood substitutes. In particular it relates to blood substitutes that may be used to sustain a euthermic subject during the course of procedures performed at body temperatures well below that which is normal for the euthermic subject.

BACKGROUND

Blood substitutes have been sought for many years to sustain the lives of human and animal subjects in the absence of the subject's own blood. In addition, such blood substitutes have been sought for the purpose of the preservation of vital organs of organ donors after their deaths.

Recently, advances in surgical methods have permitted surgeons to carry out extremely time-consuming and complicated surgical procedures. However, such procedures frequently require that the subject's body temperature is lowered to minimize the damage to the subject's vital organs, particularly the central nervous system which, because of its high metabolic demands, requires large amounts of oxygen and glucose. The potential for carrying out such complicated surgical procedures on the organs of the central nervous system and the major blood vessels, for example are severely limited due to this physiological requirement. Lowering the temperature of the euthermic subject to a temperature well below that normally maintained by the subject reduces the metabolic rate, and hence the demands for oxygen and glucose of the central nervous system as well as other vital tissues and organs.

A number of blood substitutes have been developed in the past. These blood substitutes have been used primarily for the purpose of preservation of surgically removed organs obtained from organ donors to be later used in transplant surgery. Some of the contents of these solutions are described in table 1. From this table it is readily seen that the majority of these blood substitutes are solutions of substances that readily permeate through the vasculature of the subject's or the donor's organs and are thus generally inappropriate for use in surgery performed on a living patient. Thus, the blood substitutes of Collins et al, Kidney preservation for transplantation. Lancet 1219-1222 (1969), Collins G.M., Hypothermic kidney storage. Transplant. Proc. IX:1529 (1977), Fischer et al, Flush solution 2, a new concept for one to three day hypothermic renal storage preservation. Transplantation 39:2, 122-126 (1985), Ross et al, 72-hour canine kidney preservation without continuous perfusion. Transplantation 21:498 (1976), Sacks et al, Transplantation 19:283 (1974) and Kallerhoff et al, Effects of the preservation conditions and temperature on tissue acidification in canine kidneys. Transplantation 39:5, 485-489 (1985) all consist only of low molecular weight molecules that readily traverse the capillary bed of the subject and thus are generally incapable of maintaining proper ionic or fluid balance or plasma volume. Nonetheless, Klebanoff and Phillips, Cryobiology 6:121-125 (1969) disclosed hypothermic asanguinous perfusion of dogs with 11 of 15 subject's surviving up to 95 minutes when perfused with buffered Ringer's lactate at 7.1 to 16 degrees C. (44.6-60.4 degrees F.).

Those blood substitutes that have an impermeable substance to maintain volume use human serum albumin, a mixture of plasma proteins, as the impermeate molecule to maintain blood volume. Wall et al, Simple hypothermic preservation for transporting human livers long distances for transplantation. Transplantation, 23:210 (1977). Belzer et al, Combination perfusion-cold storage for optimum cadaver kidney function and utilization. Transplantation 39:2, 118-121, (1985).

Haff et al. Journal of Surgical Research 19:1, 13-19 (1975) describe the asanguineous hypothermic perfusion of dogs using two solutions: the first a flush solution comprised of pooled delipidated homologous plasma and electrolytes and the second comprised of pooled delipidated homologous plasma, electrolytes and additional potassium chloride at a concentration of 10 mEq/liter. Haff et al also disclose the use of a pulsatile pump oxygenator and hypothermic perfusion with the above-mentioned solutions and suggest that the procedures could be used for long distance transport of cadaver organ donors and as an alternative to hypothermic circulatory arrest for blood-free intricate surgery. Haff et al, however, failed to monitor pulmonary arterial wedge pressure during the procedure, and thus exposed the subject animals to probable damage to the alveoli of the lung.

The forgoing plasma-based blood substitutes, however, have a disadvantage unforeseen at that time they were developed. If applied to human beings they would require the processing of human blood to obtain plasma or plasma proteins. However such human blood may be contaminated with life threatening virus particles such as HTLV-1, HIV or Hepatitis A or B or nonA-nonB virus. For the forgoing reasons, non-blood based blood substitutes are clearly desirable to eliminate the danger of infection associated with human blood-based products.

Bishop et al. Evaluation of hypertonic citrate flushing solution for kidney preservation using the isolated perfused rat kidney. Transplantation 25:5, 235-239 (1978) discloses a perfusion solution that included 50 g/liter dextran 40, a concentration that differs markedly from that of the blood substitute of the present invention. In addition, the electrolyte and ion concentrations differ markedly from those disclosed for the present invention. Segall et al. Federation Proceedings 44(3):623, (1985) disclose that a Ringer's lactate-based heparinized blood substitute containing 6% dextran 40 was used to lower the body temperature of hamsters prior to the circulation of cold-protective solutions, which are not disclosed, for 1 to 1.5 hours.

Segall et al (1987) disclose that a blood substitute, which included dextrose (180 mg/dl) and 25 mM HEPES, was used to perfuse a dog to 3 degrees C. when perfusion was stopped entirely. There is no disclosure of the complete composition of the blood substitute.

SUMMARY AND OBJECTS OF THE INVENTION

The invention comprises an aqueous blood substitute that can be used to perfuse and maintain a patient or donor during the course of procedures in which the patient or donor can be maintained at a body temperature substantially below that normally homeostatically maintained by the patient or donor.

The invention further comprises an aqueous blood substitute that can be used to perfuse a patient or donor maintained at a body temperature substantially below that normally homeostatically maintained by the patient or donor which aqueous blood substitute permits the patient's normal body temperature to be reestablished without debilitating damage to the patient or donor's organs.

In more detail the invention is a blood substitute that comprises an aqueous solution of electrolytes in normal physiological concentration, a macromolecular oncotic agent, a biological buffer having a buffering capacity in the range of physiological pH, simple nutritive sugar, an additional amount of magnesium ion in a concentration sufficient to block or substitute for the flux of calcium ion across cell membranes and an anticoagulant.

The blood substitute also comprises the forgoing solution and, in addition, an additional amount of a cardioplegic agent, such as potassium ion, in a concentration sufficient to entirely prevent or immediately arrest cardiac fibrillation.

Depending upon the specific application, additional materials may be included or introduced into the blood substitute. Thus for example, a non-absorbable or non-vital dye may be included or introduced into the blood substitute at stages of surgery when it is desirable to check leakage of blood from surgically repaired blood vessels. Such dyes may be added to the solution for the additional purpose of identifing the solution thereby color coding particular formulations. The color coding of solutions may be particularly desirable when the blood substitute is administered as a sequential series of solutions, as is described further herein below. Preferably such dye will be one that is eliminated from the body of the patient either metabolically or through excretion. By way of further example, it may be desirable to add contrast media to the blood substitute when it is desired to image circulatory function of the subject's vasculature. Such contrast media may be suitable for x-ray, fluoroscopic, computer assisted axial tomography (CAT scan) or magnetic resonance imaging. Such contrast media are known to radiologists and others skilled in the arts of medical imaging. Fluorescent dye may also be used. The forgoing solutions are administered to a patient or donor in an alternating sequence that is detailed further hereinbelow.

The invention also includes methods for carrying out unique life sustaining or organ sustaining procedures utilizing the blood substitute according to the invention. These procedures include methods for reducing toxicity associated with systemic chemotherapy, and reducing and controlling the effects of cerebral ischemia in trauma, surgical and stroke patients. Also included are procedures utilizing the blood substitute to increase the time period for preserving physiologically functional organs in organ donors. It is also believed that the blood substitute may be successfully used in the process of cryonically suspending individuals at temperatures below the freezing point of water and restoring such cryonically suspended individuals to a normal physiological state.

One of the objects of the invention is to provide a non-blood-based blood substitute. Another object of the invention is to provide a non-blood-based blood substitute that can be used to hypothermally perfuse living euthermic subjects without damaging the subject's vital organs, allowing the subject to be revived and restored to normal physiological and mental function. A further object of the invention is to provide a non-blood-based blood substitute that can be used to hypothermally perfuse the bodies of cadaver organ donors without damaging the organs to be donated. Yet another object of the invention is to provide a non-blood-based blood substitute that can be used in the cryopreservation of a subject in need thereof.

A still further object of the invention is to provide a non-blood-based blood substitute suitable for use at low temperature under hyperbaric oxygen conditions and is capable of transporting and exchanging oxygen for carbon dioxide in the tissues of a subject in need thereof.

Yet another object of the invention is to provide a method for the use of a non-blood-based blood substitute to hypothermally perfuse living euthermic subject without damaging the subject's vital organs and furthermore minimizing debilitating cardiac fibrillation, allowing the subject to be revived and restored to normal physiological and mental function with a minimum of cardiac stress. Yet still another object of the invention is to provide the method of specific organ directed high dose anticancer chemotherapy through the use of the blood substitute according to the invention at hypothermic temperatures. Still yet another object of the invention is to provide methods for bloodless hypothermic surgical procedures using the blood substitute according to the invention.

A further and still another object of the invention is to provide a method for the treatment of surgical shock and control of cerebral ischemia using the blood substitute according to the invention.

These and other objects of the invention will be better understood in connection with the following detailed description of the invention.

DETAILED DESCRIPTION OF THE INVENTION

The present invention is a blood substitute that comprises an aqueous solution of electrolytes at physiological concentration, a macromolecular oncotic agent, a biological buffer having a buffering capacity in the range of physiological pH, simple nutritive sugar or sugars, magnesium ion in a concentration sufficient to substitute for the flux of calcium ion across cell membranes and an anticoagulant. The blood substitute also includes the forgoing solution and a cardioplegic agent, such as potassium ion, in a concentration sufficient to prevent or arrest cardiac fibrillation.

The electrolytes at physiological concentration include ions of sodium, potassium, calcium and chloride in concentrations approximating that found in blood plasma. In addition, magnesium ion is used in excess of normal blood concentrations. In one embodiment normal electrolyte concentrations are achieved by using Ringer's lactate as the source of normal electrolytes. It is however preferred to achieve the desired concentration of electrolytes by dissolving salts of the desired ions in water, preferably distilled water.

By oncotic agent is meant substances, generally macromolecules that are of a size that is not able to leave the circulation by traversing the fenestrations of the capillary bed. Such oncotic agents are exemplified by blood plasma expanders which are known in general as macromolecules having a size sufficient to prevent their escape from the blood plasma through the circulatory capillary bed into the interstitial spaces of the body.

Human serum albumin is one well known blood plasma protein that is used to expand plasma volume. Polysaccharide blood plasma expanders are generally characterized as glucan polymers. Hetastarch (a product of American Home Products) is an artificial colloid derived from a waxy starch composed almost entirely of amylopectin with hydroxyethyl ether groups introduced into the alpha (1—4) linked glucose units. The colloid properties of a 6 % solution (wt/wt) of hetastarch approximates that of human serum albumin.

Other polysaccharide derivatives may be suitable as oncotic agents in the blood substitute according to the invention. Among such other polysaccharide derivatives are hydroxymethyl alpha (1—4) or (1—6) polymers. In general, it is preferred that the polysaccharide is one that is non-antigenic. Cyclodextrins may be suitable as oncotic agents in the blood substitute according to the invention.

Preferred are polymers of D-glucose, and in particular D-glucose linked predominantly in alpha(1—6) linkage known as dextran. In the blood substitute according to the invention it is necessary that the polysaccharide be sufficiently large so as not to escape from the capillary bed of the patient's or donor's vasculature. High molecular weight polysaccharides such as Dextran 70 having a molecular weight of about 70,000 daltons are generally less preferred because they increase viscosity of the colloidal solution and impair the achievement of high flow rates. More preferred to achieve high flow rates are polysaccharides in a molecular weight range of 30,000 to 50,000. Most preferred is Dextran 40 having a molecular weight of about 40,000. Under some circumstances, particularly in treatment of cerebral ischemia, it may be desirable to use blood substitute solutions containing higher molecular weight colloids despite their higher viscosity and relatively low flow rates. Such solutions, which may be more effective in preventing tissue swelling due to their lower rates of leakage from capillaries, may be particularly useful in the treatment of cerebral ischemia at hyperbaric oxygen tensions and for the management of edema to remove accumulated interstitial fluid. In such circumstances, it may be desirable to use higher molecular weight polysaccharide such as dextran in a molecular weight range of 50,000 to 70,000.

The concentration of the polysaccharide in the blood substitute is sufficient to achieve, when taken together with electrolytes and simple sugar discussed below, a colloid osmotic pressure approximating that of normal human serum, about 28 mm Hg. In particular when Dextran 40 is used about 6% dextran 40 (wt/wt) or about 60 grams (g) per liter (l) of water is used. Osmolality of the blood subsitute according to the invention will be in a range of about 300 to 325 miliosmoles with an osmolality of about 305 to 315 being preferred.

The blood substitute according to the invention also includes a simple sugar. Simple sugars include sucrose, fructose and glucose or dextrose, which is alpha D-glucose. Most preferred is dextrose. In general, in the blood substitute according to the invention, the concentration of the simple sugar will be in a range of from about 1 mM to about 10 mM. Glucose at a concentration of about 1.8 g per liter or about 10 mM dextrose is preferred.

Depending upon the specific purpose for which the blood substitute is to be used the concentration of the nutritive sugar may be further varied in a range between about 1mM and 1M. Thus, if the blood substitute is to be used to maintain a subject during a surgical procedure the lower concentration of dextrose of about 10 to 20 mM is used. However, if the blood substitute is used in the therapy of shock such as surgical shock the molarity of dextrose is increased above 20mM and preferably the concentration of glucose is increased to a range between about 100 mM and 1M. Higher concentrations of simple sugar, used for the treatment of surgical shock may be immediately followed by administration of blood substitute containing low concentration of simple sugar to wash out the high sugar concentration. To be avoided in the blood substitute of the invention is the use of mannitol. The use of this sugar in non-blood product based blood substitutes, when administered to a living subject, is associated with significant decreases in pH that are usually uncontrollable even with dialysis.

The pH of the blood substitute is generally maintained at a pH of about 7.8. The pH is maintained by the use of a biological buffer. Such buffers have buffering capacities in the range of physiological pH between about 7.2 and 7.9, but may have a wider range. One buffer solution suitable for use in the blood substitute according to the invention is N-2-Hydroxyethylpiperazine-N'-2-hydroxypropanesulfonic acid (HEPES) buffer which has a useful pH range between 6.8 and 8.2. Other buffers such as 3-(N-Morpholino) propanesulfonic acid (MOPS) pH range 6.5-7.9, N-tris[Hydroxymethyl]methyl-2aminoethanesulfonic acid; 2-([2-Hydroxy-1,1-bis(hydroxymethyl)ethyl]amino) ethanesulfonic acid (TES) pH range 6.8-8.2, 3-[N-tris(Hydroxy- methyl) methylamino]-2-hydroxypropanesulfonic acid (TAPSO) pH range 7.2-8.2, 4-[2-hydroxyethyl]-1piperazinepropanesulfonic acid (EPPS) pH range 7.3-8.7, and Tris[hydrolymethyl]aminomethane (THAM) may be used.

The blood substitute, according to the invention, also includes a concentration of divalent metal ion of a type and in an amount sufficient to displace or block the effects of calcium ion at the cellular membrane. Some metals that produce divalent ions, such as cadmium and beryllium, are poisonous to mammals and may not be used for this purpose. Magnesium ion is preferred and it is furthermore preferable to supply the magnesium ion by the addition of a non-chloride salt of magnesium. Magnesium sulfate is the preferred form, whereby increase in the concentration of magnesium ion can be obtained without adding chloride ion to the blood substitute. The additional magnesium ion in the blood substitute is believed to displace calcium ion in the so-called cellular membrane calcium channel. The effect achieved with magnesium ion may also be achieved through the use of drugs, the so-called calcium channel blockers, such as verapamil, which affect this same physiological mechanism. In any case about 10 mM $Mg++$ in the form of 10mM $MgSO_4$ is included in the blood substitute according to the invention.

Also included in the blood substitute, according to the invention, is an amount of an anticoagulant sufficient to prevent clotting of the patient's or organ donor's blood. Such anticoagulants are generally known and include, for example, calciparine (American Critical Care), coumadine (duPont) and heparin. Heparin is preferred and is generally available as a sodium salt. Heparin is used in a concentration sufficient to prevent blood coagulation while the blood substitute is being administered to the patient or mixed with the patients blood in the procedures described herein below. In general, a concentration of heparin sufficient for the above-described purposes is from about 1000 U/l to about 5000 U/l. A heparin concentration of about 3000 U/ml is preferred. Other anticlotting agents may also be useful, including commercially available enzymatic thrombolytics such as tissue plasminogen activator (Genentech), urokinase and streptokinase.

The blood substitute according to the invention may also be used as a blood volume expander. If the blood substitute according to the invention is used as a blood volume expander in a hypovolemic subject it may be desirable to omit anti-coagulants from the mixture. In particular, if the blood substitute according to the invention is used as a blood volume expander in a subject that is hypovolemic as a result of a wound causing blood loss it is desirable to omit anti-coagulants and or thrombolytics from the blood substitute solution so that the subject's blood clotting capability is not further imparied. Furthermore if the blood substitute according to the invention is used as a blood volume expander in a subject at nonhypothermic temperatures, the cardioplegic agent described herein below will generally be omitted so that normal cardiac function can be maintained.

The above-described solution is the first solution of a multi solution system used for the substitution of blood in a patient or donor. In one embodiment of the invention the substitution of the blood in a patient or donor is carried out in a two solution system. The second of the two solutions in this embodiment of the invention, is a cardioplegic solution that comprises the same components as described above and, in addition, at least one cardioplegic agent to reversibly arrest or prevent cardiac fibrillation in the patient or donor to which the blood substitute is being administered.

Concentrations of cations including $Mg^{++}$, $Ca^{++}$, and $K^+$ in excess of that normally found in mammalian blood are suitable for exerting a cardioplegia effect. The preferred material for inducing this effect is potassium ion. That potassium ion may be used to achieve this effect in a reversible manner is surprising in light of the well known effects of potassium ions on cardiac function. Excess potassium ion in the fluid outside of cardiac cells causes the heart to become excessively dilated and flaccid and is known to slow the heart rate. High concentrations of potassium are believed to block cardiac impulse conduction along the atrio-ventricular nerve bundle. It is conventionally believed that "[e]levation of potassium concentration to only 8 to 15 mEq./liter—two to three times the normal value—will usually cause such weakness of the heart that it will cause death." Guyton Textbook of Medical Physiology,4th edition, W.B. Saunders Company, Philadelphia (1971).

It is preferred that the concentration of potassium ion in the second solution exceed 10 mM. Preferably the potassium ion concentration is in a the range of about 15 to 45 mM. It is preferred that about 30 mM of potassium chloride is added to to yield a potassium ion concentration of about 34 mEq/liter.

The blood substitute described above may be used in a variety of specific procedures as will be further explained hereinbelow. In each of these procedures the first solution is administered after partial exsanguination of the subject patient or donor or is administered while progressively exsanguinating the patient or donor and to gradually lower the body temperature of the subject until a low temperature is reached. The second solution is used as a caridoplegic solution to block cardiac fibrillation. The cardioplegic solution may be used to maintain the subject. Alternatively, once the cardioplegic effect is achieved and the subject's body temperature lowered sufficiently that cardiac fibrillation cannot occur, the cardioplegic solution could be removed and the first solution without the cardioplegic agent could be used to maintain the subject. In any case, if the first solution is not replaced with the second cardioplegic solution during the procedure of lowering the subject's temperature, the subject's heart will fibrillate at low temperature and deplete itself of energy reserves to such an extent that restoration of the subject to normal physiological status is difficult to achieve without some compromise in the subject's health.

In general, the use of the blood substitute may be described as follows. The first solution described above without additional potassium ion, (hereinafter referred to as PreSub) is introduced via the circulatory system using cardiopulmonary bypass apparatus to replace blood at 20-30 degrees C. Preferably, a significant portion of the subject's blood will have been removed prior to introduction of PreSub. This removal of the subject's blood is useful in controlling the pulmonary arterial wedge pressure and thereby minimizes damage to the subject's lungs. Immediately after flushing with 2 blood volumes of PreSub, one volume of the second cardioplegic solution is added to the by-pass reservoir and flushed through the cardiovascular system to replace PreSub. Preferably, the cardioplegic solution has the same composition as PreSub but includes additional potassium ion as described above to control fibrillation. This solution is referred to herein after as K+PreSub. If PreSub is not replaced with K+PreSub, the heart will fibrillate at low temperatures and deplete itself of energy reserves. Experiments have suggested that this makes revival more difficult and may compromise the health of the animal or patient.

One system volume, which is defined as the volume equal to the combined volume of the subject's blood and the volume in the extracorporeal circuit, of K+PreSub should be replaced with another every 15-30 minutes. Circulation, oxygenation and core cooling using an extra corporeal membrane, hollow fiber or bubble oxygenator with a heat exchanger should continue when possible with a Swan-Ganz catheter inserted in the pulmonary artery to measure the pulmonary arterial perfusion or wedge pressure (PAW) or some other means to continuously monitor and, optionally, control left ventricular end diastolic pressure. This pressure should be kept below 10 mm Hg during the entire procedure. It is preferred that PAW be kept below 5 mm Hg during the procedure. The respiratory system should be kept at about 3-5 mm Hg of positive end expiratory pressure (PEEP). Alternately pulmonary airway pressure (PA), measured as inspiratory pressure, is monitored and kept below 12 mm Hg.

K+PreSub is used in this manner until the subject is rewarmed, or until temperature is cold enough to prevent cardiac fibrillation or is near the ice point. Upon rewarming, an amount of PreSub sufficient to remove the excess cardioplegic agent, which may be excess potassium ion, is introduced while removing K+PreSub. Generally 3 or more blood volumes of PreSub are introduced. A solution of blood, preferably the subject's own blood which was initially removed, diluted by PreSub is introduced into the subject. As rewarming continues, the subject's heart is stimulated if necessary, using electric defibrillation and also if necessary, anti-arythmics such as lidocaine and cardio-stimulants such as dopamine and epinephrine. More blood or the subject's own packed cells concentrated from effluent previously removed is added back to the subject's circulation. Surgical wounds are closed and the patient is allowed to revive and is treated in intensive care as necessary.

In a more preferred embodiment of the invention the blood substitute comprises four solutions that are systematically administered to the subject or patient sequentially. The solutions are preferably administered to the subject when the subject's body temperature has already been lowered to a point substantially below normal but prior to the induction of cardiac fibrillation due to hypothermia. In larger mammals in the range of 70 to 130 kilograms this temperature may be in a range of about 27 to 30 degrees C. and in smaller mammals in the range of 10 to 30 kilograms this temperature may be in a range of about 20 to 25 degrees C.

The first of the four solutions is the base solution and comprises water, electrolytes including magnesium ion and calcium ion in physiological concentration, a macromolecular oncotic agent, a biological buffer effective at physiological pH, simple sugar, and potassium chloride in a concentration range of 4-5 mM. The base solution preferably uses the simple sugar glucose in a concentration range of from 0 to 5 mM. In small mammals, the glucose concentration may be in the high end of the range as glucose utilization is significant during hypothermia. In addition the base solution also preferably includes about 25mM $NaHCO_3$ as a buffer in addition to HEPES buffer and $MgSO_4$ in a range of 1-2 mM.

The second of the four solutions is a cardioplegia induction solution which includes potassium chloride in a concentration sufficient to immediately stop the contraction of the subject's heart muscle thereby preventing hypothermia induced cardiac fibrillation when the solution is administered prior to the induction thereof. The concentration of potassium is in a range of 25-45 mM in the cardioplegia induction solution and a concentration of 34 mM KCL is preferred. The cardioplegia induction solution comprises the same components as the base solution however no $NaHCO_3$ is included. The buffering effect of $NaHCO_3$ is not required since the enzyme carbonic anhydride found in erythrocytes is removed when the subject or patient is exsanguinated prior to and during the administration of the base solution. The concentration $MgSO_4$ in the cardioplegia induction solution is increased about tenfold to about 10 mM; however the concentration of $CaCl_2$ is decreased to about 1.5 Mm. The concentration of glucose is about 10 mM. The molarity of the solution is maintained in the range of 305 to 314 mM.

The third of the four solutions is a cardioplegia maintenance solution. This solution has the same composition and concentrations as the cardioplegia induction solution; however, the concentration of potassium chloride is in a range of 15-20 mM, and is preferably about 18 mM.

The fourth of the four solutions is a recovery solution. This solution has the same composition as the base solution but, the concentration of potassium chloride is in a range of 6-10 mM. Preferably the concentration of potassium chloride is 7 mM. The amount of potassium chloride in the recovery solution is calculated to rapidly reconstitute potassium ion depleted during the procedure. The recovery solution is administered to the subject during rewarming. It has been observed that potassium ion is significantly depleted in subjects during rewarming from hypothermic temperatures. The concentration of potassium chloride in the recovery solution is calculated to replace and maintain potassium ion in near physiologic concentrations so that regular cardiac contraction can be obtained during rewarming but while the subject is still hypothermic. If concentrations of potassium ion higher than those necessary to obtain near physiologic concentrations of potassium are used, regular cardiac contraction is not obtained until the subject's temperature is substantially higher and ischemic damage may result. Optimally, in small mammals in the range of 12 to 30 kilograms, while recovery solution is being used regular cardiac contraction may be recovered at temperatures between 15 and 22 degrees C. In larger mammals regular Cardiac contraction may be recovered at somewhat higher temperatures between 20 and 27 degrees C.

An anticoagulant such as calciparine, coumadine or heparin or a thrombolytic such as tissue plasminogen activator (Genentech), urokinase and streptokinase is generally included in some or all of the above-described for solutions. Heparin sodium is preferred and is used in a concentration sufficient to prevent blood coagulation while the blood substitute is being administered to the patient or mixed with the patients blood in the procedures described herein below. In general, a concentration of heparin sufficient for the above-described purposes is from about 1000 U/l to about 5000 U/l. A heparin concentration of about 3000 U/ml is preferred.

The solutions of the four solution system blood substitute according to the invention may also be used as a blood volume expander in a hypovolemic subject, however it may be desirable to omit anti-coagulants or thrombolytics therefrom, particularly, if used as a blood volume expander in a subject that is hypovolemic as a result of bleeding. Furthermore if the blood substitute according to the invention is used as a blood volume expander in a subject at non-hypothermic temperatures, the cardioplegic agents described herein will generally be omitted so that normal cardiac function can be maintained.

In general the four solution system may also be used in a variety of specific procedures as will be further explained hereinbelow. In each of these procedures the base solution is administered after partial exsanguination of the subject, patient or donor or is administered while progressively exsanguinating the subject, patient or donor and to gradually lower the body temperature of the subject until a low temperature is reached. The second solution, the cardioplegia induction solution is administered to the now hypothermic subject to prevent or arrest cardiac fibrillation. In any case, if the base solution is not replaced with the cardioplegia induction solution during the procedure of lowering the subject's temperature, the subject's heart will fibrillate at low temperature and deplete itself of energy reserves to such an extent that restoration of the subject to normal physiological status is difficult to achieve without some compromise in the subject's health. Once the cardioplegic effect is achieve with the second solution and the subject's body temperature lowered sufficiently that cardiac fibrillation cannot occur, the cardioplegia induction solution is removed and replaced with the cardioplegia maintenance solution and the subject is maintained with this solution until it is desired to revive the subject. The cardioplegia maintenance solution is replaced with the fourth solution, the recovery solution and the subject is rewarmed and revived as described below.

In more detail, using the four solution system, the subject is anesthetized, prepared and monitored in the same manner for PA and PAW as described above for the use of the two solution system. The subject's body is placed on a bed of ice or immersed in an ice bath and the body temperature is gradually lowered. Prior to the introduction of the base solution, but after the body temperature of the subject has been lowered to a point before cardiac fibrillation occurs, a substantial volume of the subject's blood is removed using sterile technique and placed preferably in sterile cold storage on ice. This whole blood can be reintroduced during the revival, rewarming and recovery period in lieu of heterologous transfusion.

The extracorporeal pump and oxygenator is primed with base solution pre-chilled to approximately 20 degrees C., purged of bubbles, and at least one volume (each volume approximately equal to the circulatory volume of the subject) of the ice cold solution is circulated through the subject while monitoring PAW in the desired range. As base solution is introduced fluid volume and PAW are maintained by collecting excess volumes of fluid. The collected effluent may also be retained and the blood cells collected therefrom by known means such as centrifugation. The blood cells so collected may be reintroduced into the subject during the revival, rewarming and recovery period as well. The subject's core temperature is monitored and at a substantially hypothermic temperature, but one above that at which cardiac fibrillation caused by hypothermia usually occurs in subjects of the size and type undergoing the procedure, at least one system volume of the cardioplegia induction solution is introduced into the subject to rapidly cause cardiac arrest. (Whenever one begins to introduce one of the the solutions of the blood substitute into the subject, care is taken not to dilute the solution being introduced with solution remaining in the fluid reservoir of the pump circuit. Excess solution in the reservoir is removed from the reservoir or circulated through the subject before a subsequent solution is introduced.) In general it is preferred to introduce the cardioplegia induction solution before spontaneous hypothermia induced cardiac fibrillation occurs so that cardiac arrest is obtained without any fibrillation. Of course, in the event that cardiac fibrillation occurs during cooling of the subject with the base solution, the cardioplegia solution may be introduced immediately.

When cardiac arrest is accomplished, the cardioplegia solution is removed while the cardioplegia maintenance solution is introduced. In general at least three system volumes of this solution is circulated. During the period when the cardioplegia maintenance solution is circulated, the hematocrit of the subject is monitored. It is preferred to introduce additional cardioplegia maintenance solution and to remove an equivalent amount of cardioplegia maintenance solution from the subject whenever the subject's hematocrit reaches a value of 2 or greater, thereby maintaining the subject's hematocrit below 2. In this manner blood cells sequestered in the subject's body may be progressively removed and a hematocrit approaching zero can be maintained during the procedure. In this manner the blood substitute according to the invention is used to essentially completely flush blood from the subject's circulation. This progressive removal of sequestered blood cells during the period when the subject is being maintained under hypothermic conditions, which is accomplished by monitoring the hematocrit, may be important in obtaining successful recovery of the subject during and after the warm up and post procedure phase. It is believed that even small amounts of blood circulated at low temperature can cause significant problems, such as pulmonary leucocytosis, on recovery.

The pH of the cardioplegia maintenance solution circulating in the subject is also monitored to remain in a range of 7.3 to 7.7, as measured at 37 degrees C. with no correction for the actual temperature of the solution when it is in the subject. It is preferred to introduce additional cardioplegia maintenance solution and to remove an equivalent amount of cardioplegia maintenance solution from the subject whenever the pH falls or rises outside this range thereby maintaining the subject's pH within the 7.3 to 7.7 range.

Recovery of the subject starts with replacing the cardioplegia maintenance solution with the recovery solution. A volume of the recovery solution sufficient to completely wash out the cardioplegia maintenance solution is used. In general at least 3 volumes each approximately equivalent to the subject's blood volume are used. After sufficient recovery solution has been circulated to wash out the cardioplegia maintenance solution, rewarming of the subject is initiated. It is preferred to maintain a 7 to 10 degree C. difference between the core temperature of the subject and the recovery solution added to the system during recovery. When the subject's core temperature reaches approximately 9 to 10 degrees C., whole blood is added until the hematocrit reaches approximately 20 and temperature is in the range of 10-20 degrees or the temperature at which cardiac activity starts. If fibrillation occurs it may be necessary to defibrillate by electro-stimulation or other known means. Ventilation of the subject is restarted soon after cardiac activity has been reestablished if the subject does not reestablish breathing spontaneously. Surface warming may be started at this point and blood is added until the hematocrit reaches 20 to 40. During the rewarming phase pH may drop significantly, and physiological pH of 7.3 to 7.4 is reestablished by slow addition of a solution of $NaHCO_3$ alone or in conjunction with placing the subject on dialysis until pH stabilizes.

The following examples are intended by the inventors to be merely illustrative and are not considered to be limiting of the invention claimed hereinbelow.

EXAMPLES

Example 1: Preparation of Solutions in the two solution system

| PreSub contains per liter: | |
|---|---|
| Dextran 15 40 | 60.0 g |
| HEPES Buffer | 6.0 g |
| Dextrose | 1.8 g |
| MgSO4 | 1.2 g |
| Heparin (10,000 U/ml) | 0.5 ml |
| K + PreSub contains per liter: | |
| Dextran 40 | 60.0 g |
| HEPES Buffer | 6.0 g |
| Dextrose | 1.8 g |
| MgSO4 | 1.2 g |
| KCl | 2.2 g |
| Heparin (10,000 U/ml) | 0.5 ml |

The pH is brought to 7.8 by addition of 3.0–4.0 M NaOH.

Preparation of 30 liters of solution is done as follows:

To prepare PreSub, 1800 g of Dextran 40 are added to 27 liters of Ringer's lactate placed in 50 liter graduated carboy with a spigot at the bottom for draining off liquid. A mark should be made at the 30 liter level by adding water using a 2000 ml graduated cylinder. The carboy is placed on a magnetic stirring platform and a magnetized mixing stone is added to the carboy. When the Dextran 40 has dissolved, 180 g HEPES buffer (Sigma) is added, followed by 54 g dextrose and 36 g $MgSO_4$. The pH is brought to 7.8 by slow addition of 3M NaOH, with stirring and adjustment with 3 M HCl if necessary, while constantly monitoring the pH with a pH electrode. When a constant pH of 7.8 is achieved 15 ml of 10,000 U/ml heparin is added, and the total quantity of solution is increased to 30 liters by adding Ringers Lactate. The resulting solution is stirred and 15 liters are removed, (pre-filtering is optional to remove any remaining solids) and filtered through 0.2 micron filters into sterile containers.

To prepare K+PreSub, 33.3 g KCl is added to the remaining 15 liters of unfiltered PreSub and stirred until the salt dissolves. The solution is then optionally pre-filtered and sterile filtered as described above.

Example 2: Protocol for substitution of a canine subject's blood for 2 hours at 10 degrees Centigrade or lower.

40 l of sterile filtered PreSub and 16 l of sterile filtered K+PreSub, prepared as described in Example 1, are stored packed in ice. An approximately 40 kg experimental animal is weighed and injected intravenously into the cephalic vein with 20 cc of 2.5% Surital. An endotracheal tube will be inserted and the animal ventilated at 25 breaths per minute with an inspiration-expiration ratio at 1:3, and the stroke volume at 700 ml. Respiration is maintained with 100% $O_2$ containing 1% of an azeotropic mixture of ether and halothane (flether). The subject's body is shaved as necessary for improved heat transfer and aseptic surgery.

Following preparation, the subject is placed on the operating table. The flether concentration in the anesthetic mixture is increased to 2% immediately prior to surgery. An incision approximately 10 cm long will be made with a scalpel a few cm to the right of the midline of the neck through the skin and down to the underlying muscle layer. An electric scalpel will be used to cut through the muscle layer. The concentration of flether will be increased briefly to 2.5% if required to maintain adequate anesthesia and then reduced to 2%.

The right jugular vein will be dissected out and the vein cannulated with a 24 French venous cannula. The carotid artery will be dissected free and cannulated with a 14 French arterial cannula. An incision will be made in the region of the right femoral artery with the electric scalpel and the right femoral artery will be dissected out and catheterized to monitor arterial blood pressure. Heparin sulfate is administered.

A Terumo Hollow Fiber Oxygenator with an integrated heat exchanger, Capiox II 43, will be incorporated in the perfusion circuit. The circuit will also include a roller pump. A prime volume of blood substitute will be added to the perfusion circuit.

The subject will be heparinized with a solution containing 35 mg of heparin at a specific activity of 10,000 U/mg. To measure physiological conditions of the subject, a rectal thermistor probe is sewn in place. A Swan-Ganz (S-G) Flow-Directed Thermodilution Catheter, size 7 F, 110 cm., supplied by Edwards Laboratories, will be introduced into the right jugular vein. EKG leads will be applied, two on either side of the chest and one on the right leg.

Rectal temperature will be recorded. Pulmonary arterial pressure, as measured through the S-G catheter, will be recorded and maintained below 10 mm Hg. Pulse pressure will be recorded utilizing a pressure transducer connected to the femoral artery from which mean arterial pressure (MAP), and systolic and diastolic pressure will be recorded.

Following completion of the above preliminary preparations, baseline pulse pressure, temperature, EKG, and pulmonary arterial pressure are recorded. A 5 ml sample of femoral arterial blood is drawn and blood chemistry and gases are obtained.

The subject will then be lowered into an ice-water bath and samples of arterial blood will be obtained at body temperatures of 35, 30, 25, and 20 degrees C. Blood gases and pH will be analyzed immediately on a blood gas analyzer. Hematocrit will be ascertained by centrifugation and plasma protein will be determined by refractometry. Blood samples will be centrifuged and used to measure plasma electrolytes and comprehensively determine blood chemistry and enzymes. The respirator is maintained at 7 mm Hg of PEEP. At 33 degrees C., the flether mixture will be reduced to 1.5%, at 30 degrees C. to 1.4% and as the subject's body temperature lowers to 20 degrees C., the flether concentration is reduced to zero. Respiratory tidal volume will also be reduced to 15 ml/kg body weight at 25 degrees C., 10 ml/kg body weight at 20 degrees C., and 5 ml/kg body weight at 15 degrees C. The respirator is turned off at 10 degrees C. with the lungs maintained in 7 mm Hg PEEP.

As the subject's temperature declines to 30 degrees C. and below the pulmonary arterial wedge pressure may increase. At this point enough blood or diluted blood is removed so that the wedge pressure returns to less than 11 mm Hg. If this is not done, the subject's lungs may be damaged. When the subject rectal temperature drops to 20 degrees C., bypass is initiated. A large volume of the animal's own blood will be collected and then 4 liters of blood substitute PreSub will be circulated and the effluent collected also. The venous effluent will be collected and centrifuged to provide packed red cells for revival. Immediately after collection of the venous effluent described above, 8 liters of blood substitute K+PreSub is added to the bypass circuit and perfused through the subject. Twenty minutes later, a 5 ml sample of fluid is withdrawn from the femoral cannula and analyzed as was the blood. Four liters of K+PreSub is then added to the circuit and this procedure is repeated 3 times. Perfusion is continuous with care taken that the arterial wedge pressure not exceed 15 cm $H_2O$. Samples are also taken at 15 degrees C., 10 degrees C., 5 degrees C. and the lowest observed temperature.

Twenty minutes after the addition of the last liter of K+PreSub to the circuit, a perfusate sample is taken and 8 liters of PreSub blood substitute are perfused through. Twenty minutes following this replacement of K+PreSub with PreSub, a perfusate sample is withdrawn and another 4 liters of PreSub is circulated.

Warm up of the subject will then begin 2 hours after the initiation of bypass. A warm up gradient of about 10 degrees C. will be implemented with the heat exchanger warmed to 10 degrees C. in excess of the recorded rectal temperature.

Respiration will be renewed at 10 degrees C. and the stroke volume set according to the following schedule: 5ml/kg body weight at 10 degrees C., 10 ml/kg body weight at 15 degrees C., and 20 ml/kg body weight at 20 degrees C.

A 5 ml blood sample is withdrawn when the rectal temperature climbs to 5 degrees C. When the subject's temperature reaches 10 degrees C., the circuit is filled with diluted blood removed from the subject during washout. As the temperature climbs, more concentrated blood is added along with packed cells. Blood samples are taken at 15 degrees C., 20 degrees C., 25 degrees C., 30 degrees C. and 35 degrees C. A final sample will be taken immediately before ending the procedure.

At 20 degrees, the subject will be replaced on low levels of flether. Any blood pH base deficit will be calculated and can be corrected with an 8.4 % NaHCO$_3$ solution. During revival it may be necessary to administer a 10% CaCl2 solution, dopamine and norepinephrine.

The subject's heart may be expected to fibrillate upon rewarming, requiring electric defibrillation immediately upon observation of this condition. After recovery of spontaneous respiration, the subject will be placed in an intensive care facility for 24 hours.

Example 3: Multi-Organ Retrieval.

The brain dead organ donor is ventilated with 100% oxygen. A femoral or right radial artery is catheterized for arterial pressure determination and a femoral or radial vein will be catheterized for drug delivery. 25,000 units of heparin will be administered through the venous catheter. A S-G catheter is introduced into a terminal branch of the pulmonary artery via a jugular vein to determine pulmonary arterial wedge pressure. The body of the organ donor will be lowered into a tub of crushed ice and its temperature is lowered to 30 degrees C. At 30 degrees C. the right or left carotid or femoral artery and jugular or femoral vein are cannulated and the cannulae are connected to a cardiopulmonary by-pass circuit containing a roller pump or other appropriate pumping means and an oxygenator (with a built-in heat exchanger) of the hollow fiber, membrane or bubble type. The ventilator stroke volume is reduced as the temperature declines. As wedge pressure increases, blood is withdrawn from the femoral artery.

The temperature will then be lowered further by ice-water bath until 25 degrees C., and the circulation then placed on by-pass with the blood being hemodiluted by addition of PreSub until the hematocrit is reduced to 50% of normal. The lungs will be placed on 7 mm Hg PEEP. The pulmonary wedge pressure will be maintained below 15 mm Hg. The patient is then further chilled to 20 degrees C. or when cardiac fibrillation occurs. At this time an amount of PreSub equal to the estimated blood volume and that in the by-pass circuit (defined here as the system volume) is added. This is followed by two volumes of K+PreSub. The chilled oxygenated K+PreSub will then be circulated throughout the circuit until temperatures close to the ice point are reached. A system volume of K+PreSub will be flushed through the circuit every 20 minutes and the effluent drained. pH and blood gases will be monitored before and after each flush. When the temperature reaches the ice-point, the K+PreSub is replaced by a system volume of PreSub. At this time organs will be removed for transplantation in the order that they are needed. This method will allow organs to be retrieved and stored for 8 hours or more with no warm ischemia time.

Example 4: Use in Specific Organ-Directed High-Dose Anti-cancer Chemotherapy (SOHAC).

The patient will be treated with an appropriate anesthetic and then subjected to radial arterial and venous catheterization. An appropriate quantity of heparin is injected and pressure transducers are connected to both catheters. An S-G catheter is inserted in a terminal branch of the pulmonary artery through the right jugular vein. The patient is immersed in ice-water and the deep body temperature is reduced to 30 degrees C. The femoral artery and vein are cannulated, connected to a bypass circuit equipped with a hollow fiber oxygenator with an integral heat exchanger and a roller pump. As wedge pressure increases, blood is removed until wedge pressure is reduced to below 11 mm Hg. When the patient's temperature reaches 25 degrees C., the patient is connected to the bypass circuit and the blood volume is hemodiluted to 50% of normal hematocrit (hematocrit 20%) with PreSub. The patient will be cooled further until fibrillation occurs and then PreSub will be replaced with two system volumes of K+PreSub. The patient's temperature is lowered further to the ice-point with a fresh system volume of K+PreSub replaced every 20 minutes. When ice- point temperatures are reached (5 degrees C. and below), the vasculature of the specific organ containing a malignancy will be exposed and cannulated.

If the tumor is in the lungs, warmed oxygenated transfused blood is circulated through the bronchial artery. A catheter will be inserted in the bronchial vein and through it the effluent is removed, while the roller pump will continue to circulate ice-cold PreSub solution throughout the rest of the ice-cold body. Supplemental heating devices such as diathermy and infrared lamps can be used to heat the chest and the upper back, and when the temperature in the cardiopulmonary circuit rises to 25 degrees C. or above, very high doses of chemotherapy agents such as 5-fluorodeoxyuracil, cisplatinin or other such anti-cancer anti-metabolite are introduced into the bronchial circulation. After adequate perfusion of the chemotherapeutic agent through the lung to be treated, the lung circulation is thoroughly flushed with ice cold PreSub solution. When the temperature of the pulmonary circuit has been lowered to the ice point, and has been well flushed as determined by assay for anti-metabolite concentration, the entire bypass circuit is flushed with several volumes of PreSub, until the level of detectable antimetabolite is acceptable. At this time the patient's body temperature is elevated to 15 degrees C., when enough transfused blood (or the patients's own packed blood cells) is introduced to bring the hematocrit up to 20 %. The patients temperature is again increased to 25 degrees C., when the blood or packed cells are added until an adequate hematocrit is achieved. The cannulae are removed and surgical wounds closed. The patient will be placed on intensive care support until stabilized. This treatment will be repeated periodically until all signs of vital organ cancer disappear.

If malignant primary or secondary tumors are located in other organs such as the brain, liver, kidney, or pancreas, or localized sections of bone, the appropriate arteries and veins are cannulated to achieve localized circulation and infused with warmed oxygenated blood carrying the chemotherapeutic agent. Electromagnetic heating can be used to selectively warm the target organ containing the malignancy, while the surrounding tissues and the patient's outer surfaces of the patient's body is kept protectively chilled and isolated from the limited circulation of the chemotherapeutic agent.

It may be desirable to in some cases to perform the above procedure as described above except that after infusion with high doses of the chemotherapeutic agent, the organ is perfused free of chemotherapeutic agent with warmed oxygenated blood, then with ice-cold PreSub and chilled again to the ice point. The patient will then be re-warmed as previously described.

Example 5: Use in Bloodless Surgery.

The patient will be surgically prepared, perfused and chilled to the ice-point as described in the previous example. The surgical field is exposed and the surgical procedure is carried out while the patient is being perfused with PreSub solution. Surgical procedures such as surgery of major blood vessels such as the aorta, removal of angiomas, atherosclerotic blockages, thrombi or foreign objects as a result of trauma will be accomplished with greater precision because the surgical field will not be obscured by the patients blood. Furthermore, because the patients temperature is substantially lowered, delicate surgery can be accomplished with less time constraint. At the end of the surgical procedure, the patient will be rewarmed or re-transfused with his own blood initially drained immediately before the bypass as well as the patient's own packed red cells centrifuged from collected venous effluent. Optionally at the end of surgery and prior from removing the patient from bypass, a non-toxic dye that is visible, or contrast media will be introduced into the circulating PreSub to ensure that all the blood vessels are surgically closed and that there will be minimal blood loss when blood is re-infused.

Example 6: Use in Treatment of Surgical Shock.

The patient in surgical shock is placed on bypass and his body temperature is lowered to the ice-point as described in example 3. The PreSub solution containing high molarity simple sugars in a concentration of 0.1 to 0.3 M or greater will be circulated under hyperbaric oxygen conditions so that brain swelling is reversed. Temperature is slowly raised in hyperbaria (at greater than 1 and up to about 3 atmospheres of oxygen) until euthermia is established. Whole blood will be gradually reinfused while intracerebral pressure is monitored. Oxygen pressure will be slowly lowered until atmospheric conditions are reestablished.

Example 7: Use in Cerebral Ischemia.

The post-ischemic patient will be placed in a hyperbaric oxygen chamber, placed on bypass and cooled and blood is substituted with K+PreSub to reverse brain swelling. The patient will be revived using the basic procedure described above in example 6.

Example 8: Use in Medical Imaging.

The patient will be prepared as described in Example 6, but at the ice-point, high concentrations of contrast medium which would be toxic a normal temperature but are safe when the patient is sustained at a low metabolic state 0 degrees C., is added to the circulation to improve medical imaging techniques such as CAT, PET and MRI scans. In some cases tumors located by such scanning can be removed surgically or by SOHAC technique as describe above, or by computer-focused radiation aimed at targets illustrated and computer-identified by contrast medium concentration and distribution.

Example 9: Use in Cryo-preservation.

1. Preparation of solutions

A. Glycerol-containing cryoprotectant (GlyPro)—K+PreSub is prepared as described above in Example 1. Prior to sterile filtration 1574 ml of 100% reagent grade glycerol is added to 20 l of unfiltered K+PreSub and the solution is stirred. Seven liters of the solution are removed and sterile filtered into sterile bottles which are sealed, packed in ice and refrigerated.

B. Glucose and Glycerol-containing cryoprotectant (GluGlyPro)—To the remaining 14 liters of unfiltered GlyPro 2.9 kg of dextrose is added. When the dextrose has dissolved, 7 l are sterile filtered and sealed into 1 l bottles which are cold stored.

C. Propanediol-Sucrose-GluGlypro—To the remaining 9 liters of unfiltered GluGlyPro, 650 ml of 1,2propanediol and 3.7 kg sucrose is added. When the sucrose dissolves, the solution is sterile filtered into sterile bottles which are sealed and cold-stored.

2. Procedure for cryopreservation of a subject.

If possible prior to death a large vein in the subject's forearm will be cannulated with a 18 gauge angiocath having a 3-way stopcock. The cannula will be kept open with a saline drip. The cannula will be used for administration of heparin and other drugs after death.

If possible the patient is placed on a respirator and ventilation will be maintained. If the preceding steps have not been taken prior to death of the patient they will be taken immediately after death is pronounced.

Immediately after death the patient is packed in ice or immersed in cold water. 350 U/kg heparin is injected intravenously or added through the i.v. catheter. Ventilation using an endotracheal tube or mask attached to a respirator administering 100% 02. Manual CPR with 120 compressions per minute and 12 breathes per minute may be used in the absence of a respirator.

The sternum is exposed and split with a bone saw. The pericardium is exposed with a retractor and the heart is manually compressed 60–100 times per minute. When an arterial transducer is in place, the pressure is kept as high as possible (at normal body temperature pressure should be kept above 60 mmHg. Pressure is reduced as the patient temperature drops.

The right radial artery is catheterized and a 3 way stopcock attached if not previously done. Arterial blood is sampled for pH and $O_2$ measurement and the catheter attached to a pressure transducer and pressure monitor. The left radial vein is catheterized to monitor central venous pressure, attached to a 3-way stopcock and the venous pressure monitored with a pressure transducer and monitor.

The aorta is cannulated using a 14 French arterial cannula and the atrial appendage is cannulated using a 24 French venous cannula. The bypass circuit is filled with PreSub, taking care to remove all bubbles from the system. The patient is placed on bypass using ice cold PreSub. Right atrial pressure is monitored by inserting a catheter into the right atrium and connecting it to a pressure monitor.

An alternative approach is via the femoral veins and arteries. An incision is made into the right thigh to expose both the right femoral vein and artery, and 14

French cannula is inserted into the right femoral artery and secured. The bypass circuit is attached to the cannula and PreSub is circulated into the patient to increase pressure and vein diameter. A 24 French cannula is inserted into the femoral vein.

In both the open chest and femoral approaches, the venous cannula is connected to a circuit which includes an oxygenator of the bubble, membrane or hollow fiber type, a heat exchanger and a roller pump. The circuit also includes a reservoir, a drain and is also connected to the arterial cannula, allowing fluids to be added, and effluent to be drained, as well as providing, when required the means for administering drugs.

In the absence of a thoracotomy, a S-G catheter may be used to obtain pulmonary arterial wedge pressure. The catheter is inserted through the right jugular vein into the right side of the heart and the tip inflated when it is in place in a branch of the pulmonary artery. The S-G catheter is attached to a monitor and perfusion pressure is maintained below 20 mm Hg.

When the patient has been placed on bypass, the body temperature is lowered to 20 degrees C. with ice cold PreSub. The perfusion is monitored by sampling from the radial vein and artery using 3-way stopcocks. pH, O2 and hematocrit are measured. Colloid osmotic pressure, and later cryoprotectant concentration are estimated by refractometry. pH is adjusted by addition of sodium bicarbonate solution and increased ventilatory frequency if pH is too low. Respirator stroke volume is set a 20 ml/kg body weight and when 25 degrees C. is reached it is reduced to 15 ml/kg, at 10 degrees C. 10 ml/kg, at 15 degrees C. or when by pass is initiated ventilation is stopped. PEEP is set at 10 cm H2O.

Thermocouple probes are placed in the patients rectum and mouth, and the temperature is recorded periodically. 300 mg cimetidine HCL is introduced by nasogastric tube and the stomach may be lavaged with 500 ml riopan titralac to reduce ulceration and hemorrhage.

The bladder is drained by Foley catheter.

A burr hole is made in the skull and the brain is observed for contraction or swelling while perfusing cryoprotectants. Half of the patient's blood is replaced with PreSub at 25 degrees C. and the rest is replaced at 20 degrees C. Immediately after washing out the patients blood at 20 degrees C., 5 liters of K+PreSub is added to the bypass circuit and the patient is perfused. At 5 degrees C. K+PreSub is replaced with 7 liters of GlyPro and the GlyPRo is circulated for 30 minutes. The GlyPRo is replaced with 7 liters of GluGlyPro and the GluGlyPro is circulated for one hour. The GluGlyPro is replaced with 7 liters of Propanediol-sucrose GluGlyPro and is circulate for one hour.

Additional thermocouple sensors are placed on the surface of the groin and foot. The patient's eyelids are taped closed to prevent dehydration. The cannulas are removed and the surgical wounds are sutured.

The body is placed in double plastic body bags and surrounded with dry ice. When the temperature falls to −20 degrees C. the body is covered with dry ice. The body is maintained on dry ice for 48 hours or more. The body is then placed in a sleeping bag and placed in a metal container which is closed. Using a capsule rocker a cryocapsule is moved from a vertical to a horizontal position and the metal container is placed in the cryocapsule on rails. The cryocapsule is repositioned vertically and its bottom is filled with liquid nitrogen. After 3 days the cryocapsule is filled with liquid nitrogen and the liquid nitrogen level is maintained.

Example 10—Preparation of Solutions for the four solution system

Base solution contains the following components in the indicated concentrations:

| | |
|---|---|
| Dextran 40 | 6% |
| HEPES Buffer | 25 mM |
| glucose | 5 mM |
| MgSO4 | 1 mM |
| CaCl2 | 2.5 mM |
| KCl | 5 mM |
| NaCl | 100 mM |
| NaHCO3 | 25 mM |
| Heparin | 5000 IU/l |

Recovery solution contains the following components in the indicated concentrations:

| | |
|---|---|
| Dextran 40 | 6% |
| HEPES Buffer | 25 mM |
| glucose | 5 mM |
| MgSO4 | 1 mM |
| CaCl2 | 2.5 mM |
| KCl | 7 mM |
| NaCl | 100 mM |
| NaHCO3 | 25 mM |
| Heparin | 5000 IU/l |

Cardioplegia induction solution contains the following components in the indicated concentrations:

| | |
|---|---|
| Dextran 40 | 6% |
| HEPES Buffer | 25 mM |
| glucose | 10 mM |
| MgSO4 | 10 mM |
| CaCl2 | 1.5 mM |
| KCl | 34 mM |
| NaCl | 100 mM |
| Heparin | 2000 IU/l |

Cardioplegia maintenance solution contains the following components in the indicated concentrations:

| | |
|---|---|
| Dextran 40 | 6% |
| HEPES Buffer | 25 mM |
| glucose | 10 mM |
| MgSO4 | 10 mM |
| CaCl2 | 1.5 mM |
| KCl | 15 mM |
| NaCl | 100 mM |
| Heparin | 2000 IU/l |

The base solution and recovery solution are made up by dissolving in an appropriate volume of distilled water that is somewhat less than the final volume required to achieve the above-indicated concentrations, all of the components except NaHCO3 required to achieve the above-indicated concentrations for the base solution. NaHCO3 in an amount required to achieve to above-indicated concentration is dissolved in a small aliquot of distilled water and added slowly to the other dissolved components. Sufficient water as added to achieve the desired concentration of components in the base solution and the pH is adjusted to 7.8 with 0.1 to 0.4 M NaOH. One half of the base solution is then sterile filtered into sterile flasks and stored on ice. Sufficient KCl is added to the remaining unfiltered base solution to achieve the KCl concentration required for the recovery solution and the pH is checked and adjusted if necessary. The recovery solution is sterile filtered into sterile flasks and stored on ice.

The cardioplegia induction and cardioplegia maintenance solution are made in a similar manner wherein additional KCl sufficient to achieve the concentration required for the cardioplegia induction solution is added to the reserved unfiltered cardioplegia maintenance solution and the solution is sterile filtered after adjustment of the pH if necessary.

Example 11

In this experiment an 11.4 Kilogram (kg) male beagle was chilled and blood substituted for more than 4 hours and revived. At the time of filing the application for the present patent the animal has survived in good health for 4 months.

A 20 gauge teflon catheter was placed in to the cephalic vein and the dog was anesthetized with 2.5% Surital (sodium-5-allyl-5-(1-methylbutyl)-2-thiobarbiturate, Parke-Davis). The dog was taken to the X-ray room where the ventral cervical and inguinal regions were clipped and surgically scrubbed. The dog was maintained on halothane during fluoroscopy. A Ringer's pediatric drip was established at 0.8 ml/min into the cephalic vein. The left external jugular vein was exposed through a 2 cm skin incision and a 7 F Swan-Ganz catheter was advanced with fluoroscopy through the right heart and into the pulmonary artery. The balloon cuff of the catheter was inflated to measure PAW.

The dog was removed to the O.R. and placed on a Harvard respirator. The respirator was set at 16 breaths per minute with a 1:2 inspiratory: expiratory ratio. The tidal volume was initially set a 200 ml. Anesthesia was maintained with flether, and 100% Oz as the carrier gas. The concentration of flether varied from 1.2%–0.5%. titrated to the animal's reactivity and, in general, lowered with the deep body temperature.

The left femoral fossa was surgically scrubbed, the left femoral artery was identified, isolated through a 1.5 cm skin incision and a 5F NIH catheter was placed into the artery for monitoring systemic arterial pressure. The right external jugular vein and carotid artery were isolated in the cervical region. Heparin (2371 Units) was intravenously administered to the dog and a 12F infusion cannula (Bard) was placed into the carotid artery. A 16F cannula was fenestrated and placed through the jugular vein and into the right atrium.

All air bubbles were removed from the arterial supply line and the dog was connected to the bypass circuit. The dog's circulatory system remained isolated form the bypass circuit by cross clamps. A thermistor was attached to a gastric tube approximately 6 cm form its end) and the stomach tube/thermistor place in the stomach and thoracic esophagus respectively. Five ml of Maalox antacid was infused into the stomach. Azium (dexamethasone) was administered i.v. (22.8 mg). A 4 limb lead EKG was connected to the dog and the dog was immersed in the ice bath.

As the dog cooled, PA and PAW were never allowed to exceed 12 mm Hg and 10mm Hg, respectively.

The cardiopulmonary bypass circuit consisted of a William Harvey, H-400, infant hypothermia bubble oxygenator/heat exchanger, flow meter and roller pump and a second heat exchanger, a SciMed pediatric (model P-7-14). The bypass circuit was primed with 2000 ml of base solution (oxygenator contained 1375 ml). After 1 hour and 17 minutes of cooling, the dog's temperature was reduced to 21 degrees C. Five hundred ml of blood was exsanguinated into a sterile container to make available the dogs own whole blood during revival. The cross clamps were removed and chilled base solution (5 mM K+) was infused simultaneously with the whole blood removal. The portion of the venous effluent containing substantial concentrations of whole blood ( 450 ml) were saved for warm-up, the rest discarded.

Two minutes later, the dog's temperature was 19 degrees C., and 2 liters of cardioplegia induction solution (34mM K+) followed immediately by 1 liter of cardioplegia maintenance solution (15mM K+) was perfused through the dog replacing the previous perfusate, which was drained and discarded. Cardiac arrest occurred and $O_2$ ventilation was discontinued.

During the following 4 hour period the dog's temperature continued to fall, reaching a minimum of 1.6 degrees C. the dog's hematocrit remained below 7. Repeated blood gases, pH, electrolytes, and select serum chemistries were determined throughout the study.

Warm up was initiated 4 hours and 20 minutes after chilled blood substitution began. Just prior to warm-up, 3 liters of a recovery solution (8mM K+) was added to the bypass circuit, replacing its former contents.

When the temperature climbed to 7.5 degrees C., 750 ml of whole blood were exchanged, the effluent discarded. Shortly afterward, when the temperature reached 10.5 degrees C. the heart started beating. Another 250 ml of whole blood were quickly added.

When the temperature reached 12 degrees C., ventilation at 25 breaths per min with 100% $O_2$ was resumed. The tidal volume was started at 100 ml and increased later to 190 ml. Azium (22mg) was added i.v.. When the temperature climbed to 20 degrees C., respiration was observed. 8.4% $NaHCO_3$ was added (30 ml). The temperature approached 30 degrees C. during the next 20 minutes, and a whole blood drip was instituted. This raised the hematocrit first to 20, then to 25. An additional 55ml of 8.4% $NaHCO_3$ were added.

The animal was weaned from bypass. Both arterial and venous cannulas were removed from the blood vessels, which were ligated with 3-0 silk. The skin incisions were closed with 3-0 silk employing a simple interrupted suture pattern. The Swan-Ganz catheter and the femoral arterial cannulas were left in overnight to allow measurement of PAw and MAP. Gentamicin (23mg) was administered slowly, and g of ampicillin was injected subcutaneously. The dog was maintained on a blood drip and an additional 10 ml of 8.4% $NaHCO_3$ was administered.

Within 4 hours of rewarming, the animal could react to stimuli. Shortly afterward, it opened its eyes. The dog was placed in the ICU and administered $O_2$ by face mask overnight. It took continuous administration of blood for several hours in the ICU to prevent sharp falls in hematocrit and plasma protein. Period of hyperventilation and hypertension were observed. The animal responded positively to petting, and even more so to 25 mg of valium administered the next morning. Lassix (2 ml) was given the following morning.

Recovery was slow, with the animal unable to stand for the first month, although its sensorium appeared unimpaired. After this period, the dog could stand and walk and within two months it was nearly completely recovered. By four months after the procedure described above, it was normal and functioned as a regular household pet, despite the fact that it was below 10 degrees C. for 4 hours and 20 minutes with a hematocrit between 2-6.

It is now believed that an excessive amount of NaHCO$_3$ may have been used leading to impairment of the lungs. The four hour period during which sequestered blood was allowed to emerge from the animal and circulate through the bubble oxygenator and roller pump is now suspected of further damaging the lungs, which received some protection by the administration of azium before cooling and immediately after the onset of warm up.

We claim:

1. A blood substitute capable of maintaining a subject and its organs at temperatures below 20° C. comprising a base solution comprising water, electrolytes in physiological concentration, a macromolecular oncotic agent, a biological buffer effective at physiological pH, simple sugar, and potassium ion in a concentration range of 4-5 mEq,
   a cardioplegia induction solution comprising said base solution and wherein the concentration of potassium ion is in a range of 25-45 mEq,
   a cardioplegia maintenance solution comprising said base solution and wherein the concentration of potassium ion is in a range of 15-45 mEq,
   and a recovery solution comprising said base solution and wherein the concentration of potassium ion is in a range of 6-10 mEq.

2. The blood substitute of claim 1 wherein the macromolecular oncotic agent comprises an impermeate polysaccharide.

3. The blood substitute of claim 1 wherein said polysaccharide is dextran.

4. The blood substitute of claim 3 wherein said dextran is at a concentration sufficient for the blood substitute to achieve a colloidal suspension having an oncotic pressure essentially a colloidal suspension having an oncotic pressure essentially equivalent to mammalian plasma.

5. The blood substitute of claim 4 wherein said dextran is dextran 40.

6. The blood substitute of claim 4 wherein said dextran is dextran 70.

7. The blood substitute of claim 1 wherein said base solution and said recovery solution but not said cardioplegia induction solution and said cardioplegia maintenance solution, further comprise about 25 mM NaHCO$_3$.

8. The blood substitute of claim 1 wherein said base solution and said recovery solution but not said cardioplegia induction solution and said cardioplegia maintenance solution, comprise glucose in a concentration from 0-5 mM.

9. The blood substitute of claim 1 wherein said cardioplegia induction solution and said cardioplegia maintenance solution, comprise about 10 mM glucose.

10. The blood substitute of claim 1 wherein said base solution and said recovery solution but not said cardioplegia induction solution and said cardioplegia maintenance solution, comprise magnesium ion in a concentration of about 1-2mEq.

11. The blood substitute of claim 1 wherein said cardioplegia induction solution and said cardioplegia maintenance solution, comprise magnesium ion in a concentration of about 10 mEq.

12. The blood substitute of claim 1 wherein said base solution and said recovery solution but not said cardioplegia induction solution and said cardioplegia maintenance solution, comprise CaCl$_2$ in a concentration range of 2.5-3 mM.

13. The blood substitute of claim 1 wherein said cardioplegia induction solution and said cardioplegia maintenance solution, comprise CaCl$_2$ in a concentration range of 1.5-2 mM.

14. The method, of performing a bloodless hypothermic procedure upon a non-living euthermic subject comprising the steps of:
   (a) lowering the subject's core body temperature to a temperature above ice point and insufficient to cause cardiac fibrillation;
   (b) placing the subject's circulation on by-pass.
   (c) perfusing the subject with an amount of a first perfusate sufficient to remove essentially all of the subject's circulating blood said first perfusate comprising, water, electrolytes in physiological concentration, a macromolecular oncotic agent, a biological buffer effective at physiological pH, simple sugar, magnesium ion in a concentration sufficient to substitute for calcium ion in membrane calcium ion channels;
   (d) when the subject's temperature is substantially hypothermic but before cardiac fibrillation occurs, perfusing the subject with an amount of a second perfusate sufficient to replace essentially all of the circulating first perfusate, said second perfusate comprising, water, electrolytes in physiological concentration, a macromolecular oncotic agent, a biological buffer effective at physiological pH, simple sugar, magnesium ion in a concentration sufficient to substitute for calcium ion in membrane calcium ion channels and a cardioplegic agent in a concentration sufficient to prevent or arrest cardiac fibrillation or contraction.

15. The method of claim 14 wherein prior to perfusing the subject with said first perfusate, removing an amount in the range from ⅛ to ½ of the subject's blood.

16. The method of claim 14 wherein subsequent to perfusing the subject with said second perfusate when the subject's temperature is below that at which cardiac fibrillation or regular cardiac contraction can occur, perfusing the patient with a sufficient amount of said first perfusate to wash out the cardioplegic agent.

17. The method of claim 14 further comprising the steps of rewarming the subject, perfusing the subject with a sufficient amount of said first perfusate to wash out the cardioplegic agent, and perfusing the subject with sufficient whole blood or packed blood cells to wash out said first perfusate and raise the subjects hematocrit to about 20 at a core body temperature of about 25 degrees C. and a hematocrit to about 30 at a core body temperature of about 35 degrees C.

18. The method of claim 16 comprising rewarming the subject and perfusing the subject with sufficient whole blood or packed blood cells to wash out said first perfusate and raise the subjects hematocrit to about 20 at a core body temperature of about 25 degrees C. and a hematocrit to about 30 at a core body temperature of about 35 degrees C.

19. The method of claim 14 wherein the subject is subjected to hyperbaric oxygen tension prior to or while the first or second or first and second perfusate are administered.

20. The method of claim 17 wherein the subject is subjected to hyperbaric oxygen tension prior to or while the first or second or first and second perfusate are administered or while the subject is recovering.

21. The method of performing a bloodless hypothermic procedure upon a euthermic subject in need thereof comprising the steps of:
    (a) lowering the subject's core body temperature to a temperature above ice point and insufficient to cause cardiac fibrillation;
    (b) placing the subject's circulation on by-pass;
    (c) perfusing the subject with an amount of a first perfusate sufficient to remove essentially all of the subject's circulating blood said first perfusate comprising, water, electrolytes in physiological concentration, a macromolecular oncotic agent, a biological buffer effective at physiological pH, simple sugar, and potassium ion in a concentration range of 4–5 mEq;
    (d) when the subject's temperature is substantially hypothermic but before cardiac fibrillation occurs, perfusing the subject with an amount of a second perfusate sufficient to replace essentially all of the circulating first perfusate, said second perfusate comprising, water, electrolytes in physiological concentration, a macromolecular oncotic agent, a biological buffer effective at physiological pH, simple sugar;
    (e) after cardiac contractile activity stops replacing essentially all of said circualting second perfusate with a third perfusate comprising water, electrolytes in physiological concentration, a macromolecular oncotic agent, a biological buffer effective at physiological pH, simple sugar, and potassium ion in a concentration range of 15–45 mEq;
    (f) prior to reintroducing blood into the subject, replacing essentially all of the circulating third perfusate with a fourth perfusate comprising water, electrolytes in physiological concentration, a macromolecular oncotic agent, a biological buffer effective at physiological pH, simple sugar, and potassium ion in a concentration range of 6–10 mEq.

22. The method of claim 21 wherein prior to perfusing the subject with said first perfusate, removing an amount in the range from ⅛ to ½ of the subject's blood.

23. The method of claim 21 further comprising the steps of initiating rewarming the subject, while perfusing the subject with a sufficient amount of said fourth perfusate to wash out the third perfusate and perfusing the subject with sufficient whole blood or packed blood cells to wash out said fourth perfusate and raise the subjects hematocrit to about 20 at a core body temperature of about 25 degrees C. and a hematocrit to about 30 at a core body temperature of about 35 degrees C.

24. The method of claim 21 wherein the subject is subjected to hyperbaric oxygen tension while at least one of the first, second, third, or fourth perfusate is circulated in the subject.

25. The method of claim 14 wherein the amount and rate of introduction of any fluid into the subject is controlled by removing from the subject's circulation sufficient fluid to maintain the pulmonary arterial wedge pressure at 5 mm Hg or less.

26. The method of claim 21 wherein the amount and rate of introduction of any fluid into the subject is controlled by removing from the subject's circulation sufficient fluid to maintain the pulmonary arterial wedge pressure at 5 mm Hg or less.

* * * * *